United States Patent

Levy et al.

Patent Number: 6,087,548
Date of Patent: Jul. 11, 2000

[54] METHOD AND ASSEMBLY FOR STERILIZING CONTAMINATED WASTE

[76] Inventors: Alfred Levy, 104 rue d'Aguesseau; Guy Bettoun, 46 rue de Bellevue, both of 92100 Boulogne, France

[21] Appl. No.: 09/125,073
[22] PCT Filed: Feb. 13, 1997
[86] PCT No.: PCT/IB97/00123
§ 371 Date: Aug. 12, 1998
§ 102(e) Date: Aug. 12, 1998
[87] PCT Pub. No.: WO97/29791
PCT Pub. Date: Aug. 21, 1997

[30] Foreign Application Priority Data

Feb. 15, 1996 [FR] France ................................. 96 02096

[51] Int. Cl.$^7$ .............................. A62D 3/00; B09B 3/00
[52] U.S. Cl. ......................... 588/255; 405/128; 422/26; 588/249
[58] Field of Search ................... 405/128, 129; 588/249; 422/22, 26, 34

[56] References Cited

U.S. PATENT DOCUMENTS 4,552,720  11/1985  Baker, Sr. et al. .
4,662,516   5/1987  Baker, Sr. et al. .
4,919,569   4/1990  Wittenzelliner ................... 405/129 X

FOREIGN PATENT DOCUMENTS

WO 90/14847  12/1990  WIPO .
WO 90/15419  12/1990  WIPO .
WO 93/12841   7/1993  WIPO .

*Primary Examiner*—Dennis L. Taylor
*Attorney, Agent, or Firm*—Alston & Bird LLP

[57] ABSTRACT

The invention relates to a disposable assembly for collecting contaminated waste, comprising a heat-stable container (1), for example made of metal, in order to withstand, without deformation, the conditions, particularly the temperature conditions, of a complete sterilization of its contents, and intended for household and/or industrial refuse, and forming a chamber provided with a sealable opening (2) through which the contaminated waste (3) is introduced, and a hot-melt plastic material (11) which is meltable under the conditions, particularly the temperature conditions, of sterilization, and is arranged inside the container (1), with a sufficient mass to enclose the waste (3) in the molten plastic material, the assembly additionally including a permeable cover (15), with a filter (55), sealing the opening (2) of the container (1).

22 Claims, 2 Drawing Sheets

METHOD AND ASSEMBLY FOR STERILIZING CONTAMINATED WASTE

FIELD OF THE INVENTION

The present invention relates to an assembly for sterilizing and converting contaminated waste, and in particular contaminated medical waste, such as, for example, needles, scalpels and used syringes.

BACKGROUND OF THE INVENTION

In the field of treating contaminated waste, and in particular contaminated medical waste, it is known, for example, to use powerful incinerators or sterilization devices with which it is possible to melt the metal parts of the contaminated waste, for example needles and scalpels, with an electric arc or an electric discharge. These latter devices are relatively heavy and require a source of electrical power, such as a battery or a mains socket, and this limits their portability and their availability to hospitals. Such devices are described, for example, in documents EP-A-0 634 182, WO 94/13346 and WO 94/01153.

These devices, however, cannot generally be installed or used by health professionals such as doctors and nurses outside the hospital environment. Current legislation governing the storage and treatment of contaminated waste thus poses a constant and not inconsiderable problem for them. Indeed, the problem of the portability and functioning of any sterilization device must be taken into consideration for these health professionals, whether in general practice, for example, or in outpatient medicine.

Moreover, application WO-A-90/15419 describes a device for treating medical or contaminated waste by sterilization, this device including a container, one part of which is compressible, and inside which there is arranged at least one hot-melt compound. In a first stage, the container is heated in an oven, optionally equipped with a filter for the gases which are released during the heat treatment, so as to melt the hot-melt compound around the waste, thereby rendering the latter unrecognizable and sterile. In a second stage, the container is compressed to make it possible to enclose the cutting elements forming part of the waste to be sterilized, which elements would risk piercing the container if they were not completely enclosed.

The disadvantage of this solution is that the container forming a chamber is not integral, that is to say not sufficiently robust from a mechanical point of view, because it is deformable by compression, which fact represents a potential danger for third parties if the container were to open, for example when it was being collected by the garbage truck. Moreover, the use of a filter on the wall of the oven also poses many drawbacks, namely:

- the need to have an oven which closes hermetically in order to justify its existence;
- the need to service the filter in order to prevent it from clogging;
- the risk of accidental infection, during such servicing, by microorganisms which have been able to settle therein;
- the risk, in the event of clogging, of the assembly exploding because of too great a pressure of gases released in the chamber of the oven;
- and the inevitable pollution to the environment when the oven is opened, since it contains potentially dangerous vapors.

SUMMARY OF THE INVENTION

The subject of the present invention is therefore a sterilization and conversion assembly allowing an individual, such as a doctor or a nurse in a medical surgery, both to temporarily store the contaminated waste, including metal waste, and to safely render the waste sterile and non-reusable, by means of equipment which is simple and easy to use. The waste thus converted by the assembly according to the present invention can be disposed of with the household or industrial refuse, without risk of contamination to a third party who might come into contact with the waste thus treated.

In accordance with the invention, a disposable assembly for collecting contaminated waste is made available, comprising a heat-stable container, for example made of metal, in order to withstand, without deformation, the conditions, particularly the temperature conditions, of a complete sterilization of its contents, and intended for household and/or industrial refuse, and forming a chamber provided with a sealable opening through which the contaminated waste is introduced, and a hot-melt plastic material which is meltable under the conditions, particularly the temperature conditions, of sterilization, and is arranged inside the container, with a sufficient mass to enclose the waste in the molten plastic material, the assembly being more particularly characterized in that it additionally includes a permeable cover, with a filter, sealing the opening of the container.

The assembly according to the present invention is intended for use in a medical surgery. It follows from this use that the assembly according to the invention must be complete, and especially guaranteeing the integrity of the container under the conditions of sterilization, in order to function safely without olfactory emanation. It was not therefore acceptable to use a treatment assembly comprising a container which would allow olfactory emanations to escape into the atmosphere, or which would pose risks of accidental infection or of explosion, as in the assembly of the prior art discussed above. In the assembly of the present invention, the container, including the cover equipped with a filter, is for one-off use, which means that the problems of the prior art do not present themselves. This is because the container, closed by its cover including the filter, is simply disposed of after sterilization of the waste. This has another advantage in that the filter is also sterilized, without having to be touched, which increases the safety of the assembly.

In accordance with another object of the invention, a method for sterilizing contaminated waste is made available, said method comprising the following steps, which consist in:

introducing contaminated waste into a disposable container forming a sterilization chamber, made of a heat-stable material which is stable under the conditions, particularly the temperature conditions, of sterilization, and for the predetermined operating period of sterilization, the container containing a hot-melt plastic material which is meltable under said conditions of sterilization;

sealing the container irreversibly, before placing it in the oven, by snap-fitting a cover which includes a filter;

placing the container, containing the contaminated waste, in an oven specifically adapted to provide said conditions of sterilisation, in order to ensure complete sterilization of the contaminated waste;

heating the oven under said conditions of sterilization in such a way that the hot-melt plastic material arranged in the disposable container melts and encloses the waste, thereby making the disposable container and the waste non-reusable;

removing from the oven the container containing the waste which has been sterilized and enclosed by the hot-melt plastic material, and disposing of said container.

The cover is preferably designed to be fitted on the container in such a way as to seal it irreversibly.

The predetermined sterilization temperature is advantageously situated between 50° C. and 300° C., preferably between 200° C. and 300° C., and the predetermined duration of sterilization is between 15 and 120 minutes, preferably between 15 and 90 minutes.

In one preferred embodiment of the invention, the cover is provided with a male part, consisting of a retainer ring, which can engage irreversibly with a female part, consisting of an elastically deformable flange formed on the container.

In one preferred embodiment, the hot-melt plastic material is arranged on the inner walls of the disposable container.

In another preferred embodiment of the invention, the hot-melt plastic material is arranged en bloc on the bottom of the disposable container.

The hot-melt plastic material is advantageously a synthetic or natural resin or wax which is meltable at a temperature of between 50° C. and 300° C., preferably between 200° and 300° C., and is chosen from the group consisting of waxes, olefinic resins, phenolic resins, vinyl resins and acrylic resins and/or a mixture of these.

In one preferred embodiment of the invention, the disposable container also includes a sterilization indicator arranged outside the container. The sterilization indicator can consist of a thin plate containing a heat-sensitive color reagent whose change is visible to the naked eye, said plate being arranged on an outer wall of the container.

Advantageously, the opening is additionally sealed in a reversible manner by a lid which is integral with the container and can be moved in rotation with respect thereto, the lid itself including an opening which can be brought into register with the opening of the container in order to ensure the opening and sealing of the container. The lid preferably also includes notches for gripping cutting and/or piercing articles.

In a preferred embodiment of the invention, the assembly additionally includes an oven including means for regulating the predetermined temperature and duration of sterilization, and fixing said temperature at a range of between 50° C. and 300° C., preferably between 200° C. and 300° C., and fixing said duration at a range of between 15 and 120 minutes, preferably between 15 and 90 minutes.

More preferably, the oven includes means for locking the door of the oven during said predetermined duration, and for automatically unlocking the door once the temperature inside the oven is sufficiently low to allow the container to be handled without danger to the user.

BRIEF DESCRIPTION OF THE DRAWINGS

The present invention will be illustrated more particularly by the following detailed description of a nonlimiting example, accompanied by the attached drawings in which.

DESCRIPTION OF ILLUSTRATED EMBODIMENTS

Figure 1:
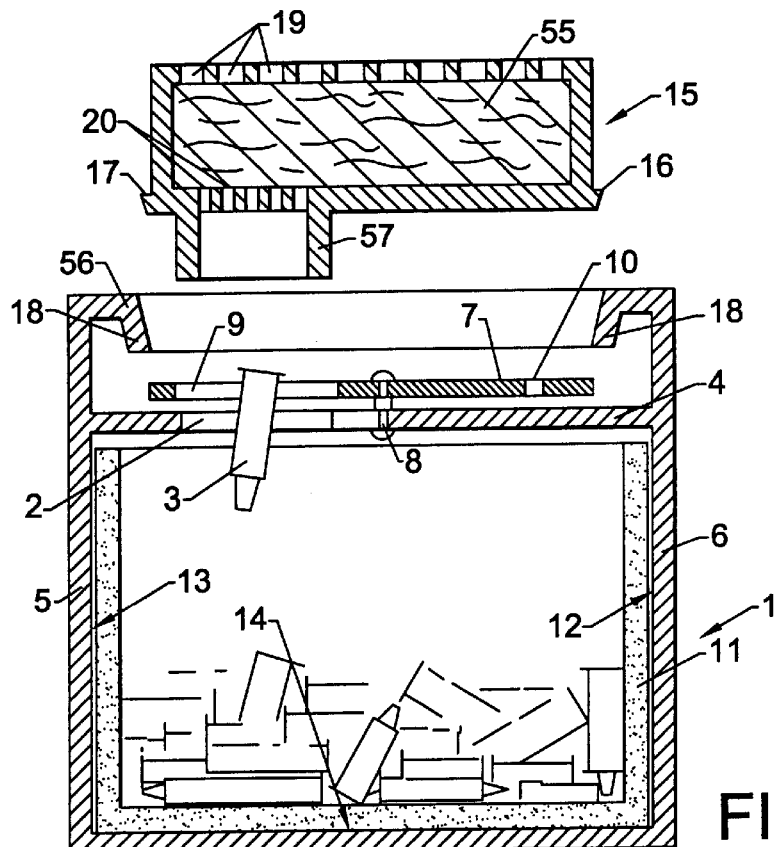
FIG. 1 represents an exploded view, partly in cross section, of an assembly according to the invention, before sterilization, the cover not being used and thus set aside.

In accordance with FIG. 1, the assembly comprises a disposable container 1 forming a sterilization chamber, equipped with a sealable opening 2 through which the contaminated waste 3 is introduced. The disposable container 1 is made of a heat-stable and leaktight material, for example of metal such as stainless steel, allowing the integrity of the sterilization system to be maintained at all stages of its use. Indeed, the container must be heat-stable and nondeformable under the conditions of sterilization, in particular at the relatively high temperatures throughout the time which is necessary and sufficient for the sterilization, but also in the cooled state. For this reason, the container will preferably be made of stainless steel having a thickness of approximately 0.26 mm and bearing the approval "Authorized for Transportation of Hazardous Substances" in accordance with the European standard of "Group I Solid". The container thus constitutes in itself an absolute barrier in terms of the cutting or piercing articles contained in its interior. The shape of the container is not very important, but it will preferably be of cylindrical or parallelepipedal shape. The opening 2 is made in the upper wall 4 of the container, or can be an attached component, fixed by crimping or welding to the side walls 5, 6 of the container. The opening 2 is preferably circular and has a diameter of between 1 cm and 7 cm, preferably 5 cm. The opening 2 also serves as an outlet for the gases released during the sterilization, as will be described hereinafter.

This opening 2 is closed by a lid 7 of the "salt cellar" type which is integral with the container 1 and can be moved in rotation relative to the latter by means of a pin 8 which passes through the lid 7 and the upper wall 4 of the container 1. The lid 7 is the form of a flat disk arranged parallel to the upper wall 4 and includes its own opening 9 which can be brought into register with that 2 of the container 1 by rotation of the lid 7, allowing access to the container for introduction of the contaminated waste and closure of the opening 2 thereof. The lid 7 is also equipped with at least one notch 10 allowing it to be gripped directly with cutting and/or piercing articles such as needles and scalpels, without handling, and thus without risk of accidental injury.

In an alternative embodiment (not shown), the waste can be introduced into the container via an opening of 1 to 10 cm in diameter, formed directly in the upper wall. This opening is designed in such a way that it is possible to introduce the waste into the container without, however, being able to remove the waste, for example by providing an opening which has a nonreturn flap. A second opening or notch can also be formed in the upper wall or the flap in order to permit gripping of cutting and/or piercing articles such as needles or scalpels.

The container 1 has, arranged within its interior, a lining 11, for example in the shape of a bucket, made of a hot-melt plastic material which is meltable at the sterilization temperature. The lining is preferably arranged in proximity to or on the inner walls 12, 13, or else simply en bloc on the bottom 14 of the disposable container 1. The hot-melt plastic material is, for example, a synthetic or natural resin which can melt at a temperature of between 50 and 300° C., and preferably between 200 and 300° C., and is chosen from the group consisting of the olefinic resins, phenolic resins, vinyl resins and acrylic resins and/or a mixture of these. One of the functions of this plastic material is, by melting, to enclose the waste and to transfer, by conduction, the sterilization temperature to the waste in such a way that this waste, even enclosed, is sterilized and converted in the molten mass of the plastic material, thereby making the waste on the one hand unidentifiable and harmless and on the other hand non-reusable. The waste is therefore made unrecognizable, which prevents a third person from identifying waste which may be psychologically troubling to the eye, and is present in the form of a solid pack adhering to the walls of the container 1, which fact eliminates the risk of its contents being scattered in the event of breakage or accidental opening.

Moreover, in order to increase the safety of use of the assembly in a medical surgery, the resin has another function, which is that of almost completely absorbing the vapors which are released by the sterilization. Thus, and in a preferred manner, the resin which has been used is a microcrystalline wax having:

a melting point of between 69 and 76° C. (according to French standard NFT-60.121);

and a viscosity at 10° C. of 7.5 to 8 cSt (according to French standard NFT-60.100).

Figure 2:
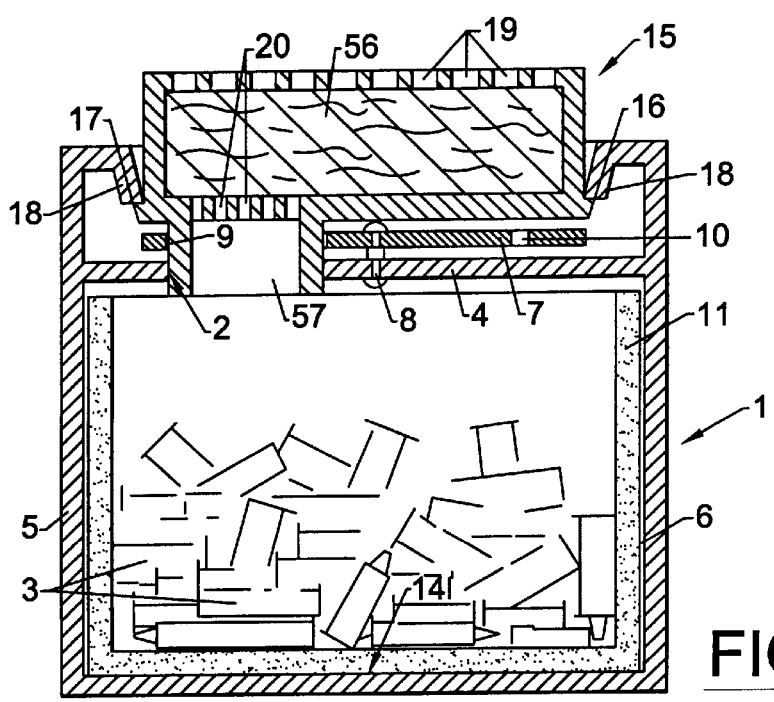
FIG. 2 represents the same assembly in cross section, ready to be sterilized, with its opening sealed in an irreversible manner by a cover forming a filter.
Figure 3:
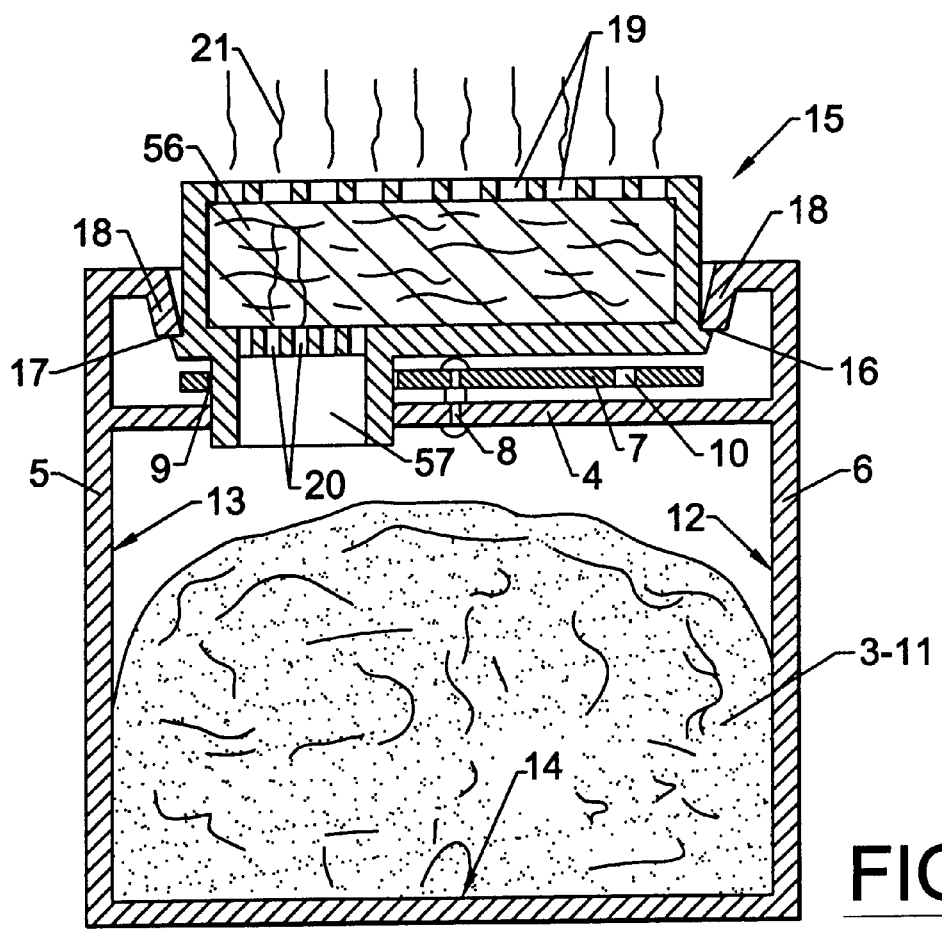
FIG. 3 represents the same assembly in cross section, after sterilization.

The assembly additionally includes a permeable cover 15 including a filter 55. This cover 15 can be of any appropriate shape, but will preferably be of cylindrical or parallelepipedal shape and will be complementary and adapted for definitive fixation to the neck 18 of the container 1, which neck 18 is formed and arranged above the upper wall 4. The filter 55 is used to treat gases released by the sterilization in such a way as to trap and retain the effluents resulting from sterilization which are toxic or harmful to the environment. It should be noted that the filter is also sterilized during the treatment, which fact increases the safety of the system. The filter is preferably made of a material which is resistant to the conditions of sterilization, for example rock wool, and not of activated charcoal like the filter used in the prior art, since the Applicant has discovered that this latter type of filter ceases to exert a filtering activity at the sterilization temperatures. The cover 15 includes a male part, comprising a retainer ring 16, which engages irreversibly, for example by snap-fitting, with a female part, consisting of a continuous flange 18 which is elastically deformable and is formed in a neck arranged above both the upper wall 4 and the opening 2. The cover 15 is equipped with openings 19, 20 formed in its upper part and in its lower part. Once the cover 15 has been fitted in the neck of the container 1, a leakproof seal is created and it is no longer possible to disconnect the one from the other, which also prevents any escape of solid material. This situation is represented by FIGS. 2 and 3, and more particularly by FIG. 3, in which exhaust gases 21 are seen escaping from the container 1 through the filter 55.

The cover 15 comprises, by way of example, but not imperatively, a lower funnel 57 which is used for indexing the cover 15 in relation to the opening 2 formed in the upper part 4 of the container 1. This funnel 57 is designed to penetrate into the opening 2, via the opening 9 in the lid 7, in the assembled and definitive position of the cover 15 in the neck 18. The passages 20 of the cover 15 establish the required communication between the funnel 57 and the interior of said cover, comprising the filter 55.

In another embodiment, the cover 15 comprising the filter 55 can be placed over the container 1 and can be screwed on irreversibly or else welded to the container using a thermosetting material arranged on the flange 18 or the retainer ring 16.

The container 1 can also be equipped with a sterilization indicator, known per se and not shown, arranged outside the container. The sterilization indicator preferably consists of a thin plate containing a heat-sensitive color reagent whose change is visible to the naked eye, said plate being arranged on an outer wall of the container, for example, by adhesive bonding. Such indicators are commercially available and are sold especially by the company Ansell Medical. These indicators guarantee the level of sterilization inside the container and are presently used in hospitals for sterilizing surgical instruments and equipment.

The sterilization assembly is associated with an oven which is not represented in the figures, because its form is that of a traditional oven, for domestic use, and does not require special comment. It simply suffices that the oven is of larger dimensions than the assembly described above, with the cover 15. The oven is specially adapted to supply a predetermined operating temperature for a predetermined length of time sufficient to ensure the complete sterilization of the contaminated waste. The oven preferably includes means for regulating the predetermined temperature and duration of sterilization, which means fix said temperature in a range of between 50° C. and 300° C., preferably between 200° C. and 300° C., and fix said duration in a range of between 15 and 120 minutes, preferably between 15 and 60 minutes. The oven can also include means for locking the door of the oven during said predetermined duration, and for automatically unlocking the door once the temperature inside the oven is sufficiently low to allow the container to be handled without danger to the user.

The method according to the invention will now be described with reference to a user, for example a doctor working in a medical surgery or having to travel around.

At the outset, the cover 15 is kept aside, so that the container 1 is directly usable, by opening or closing the opening 2 by means of the rotatable lid 7.

The contaminated waste is introduced into the container, through the openings 2 and 9, as the doctor carries out his work. At the end of the storage period authorized by law, or if the container 1 is filled before this period, the doctor closes the container 1 irreversibly by snapping the cover 15 onto the neck 18. To this end, the opening 2 is kept open by means of its being aligned with the opening 9 of the lid, through which openings the funnel 57 passes. The assembly, thus closed, is placed in the oven. The latter is then heated to about 230° C. for 15 to 120 minutes, preferably between 15 and 60 minutes, in order to sterilize the contents of the container 1 and to melt the hot-melt lining 11, thereby leaving the container and the waste sterilized and non-reusable. At the end of the predetermined period, the doctor checks that sterilization has been completed either by way of the change in color of the indicator, or, if the oven is equipped with means so allowing, by the automatic opening of the oven door. The container, thus sterilized, and its contents, having assumed the form of a solid lump amalgamating the solid waste and the hot-melt plastic material, can then be disposed of directly in the household or industrial refuse, without the need to carry out subsequent sterilization treatment and without risk to the environment.

What is claimed is:

1. A disposable assembly for collecting contaminated waste, comprising:

a heat-stable container made of a material which will withstand, without deformation, the temperature conditions of a complete sterilization of its contents, and intended for household and/or industrial refuse, and forming a chamber provided with a sealable opening through which the contaminated waste is introduced;

a hot-melt plastic material which is meltable under the temperature conditions of sterilization, and is arranged inside the container, with a sufficient mass to enclose the waste in the molten plastic material; and a permeable cover, with a filter, sealing the opening of the container and closing the chamber.

2. An assembly according to claim 1, wherein the cover is designed to be fitted on the container in such a way as to seal it irreversibly.

3. An assembly according to claim 1, wherein the cover is provided with a male part, consisting of a retainer ring, which can engage irreversibly with a female part, consisting of an elastically deformable flange formed on the container.

4. An assembly according to claim 1, wherein the hot-melt plastic material is arranged on the inner walls of the disposable container.

5. An assembly according to claim 1, wherein the hot-melt plastic material is arranged as a block on the bottom of the disposable container.

6. An assembly according to claim 1, wherein the hot-melt plastic material is a synthetic or natural resin or wax which is meltable at a temperature of between 50° C. and 300° C., and is chosen from the group consisting of waxes, olefinic resins, phenolic resins, vinyl resins and acrylic resins and/or a mixture of these.

7. An assembly according to claim 1, wherein the hot-melt plastic material is a microcrystalline wax having a melting point of between 69° C. and 76° C. (according to French standard NFT-60.121) and a viscosity at 10° C. of 7.5 to 8 cSt (according to French standard NFT-60.100).

8. An assembly according to claim 1, wherein the disposable container also includes a sterilization indicator arranged outside the container.

9. An assembly according to claim 8, wherein the sterilization indicator consists of a thin plate containing a heat-sensitive color reagent whose change is visible to the naked eye, said plate being arranged on an outer wall of the container.

10. A disposable assembly for collecting contaminated waste, comprising:

a heat-stable container made of a material which will withstand, without deformation, the temperature conditions of a complete sterilization of its contents, and intended for household and/or industrial refuse, and forming a chamber provided with a sealable opening through which the contaminated waste is introduced;

a hot-melt plastic material which is meltable under the temperature conditions of sterilization, and is arranged inside the container, with a sufficient mass to enclose the waste in the molten plastic material;

a permeable cover, with a filter, sealing the opening of the container and closing the chamber, and a lid which is integral with the container and can be moved in rotation with respect thereto for sealing the opening in a reversible manner, the lid including an opening which can be brought into register with the opening of the container in order to ensure the opening and sealing of the container.

11. An assembly according to claim 10, wherein the lid also includes notches for gripping, cutting and/or piercing articles.

12. An assembly according to claim 1, wherein said assembly additionally includes an oven including means for regulating the predetermined temperature and duration of sterilization, and fixing said temperature at a range of between 50° C. and 300° C., and fixing said duration at a range of between 15 and 120 minutes.

13. An assembly according to claim 12, wherein the oven includes means for locking the door of the oven during said predetermined duration, and for automatically unlocking the door once the temperature inside the oven is sufficiently low to allow the container to be handled without danger to the user.

14. A method for sterilizing contaminated waste, comprising the following:

introducing contaminated waste into a disposable container forming a sterilization chamber, made of a heat-stable material which is stable under the conditions, particularly the temperature conditions, of sterilization, and for the predetermined operating period of sterilization, the container containing a hot-melt plastic material which is meltable under said conditions of sterilization;

sealing the container, before placing it in the oven, with a cover which includes a filter;

placing the container, containing the contaminated waste, in an oven specifically adapted to provide said conditions of sterilization, in order to ensure complete sterilization of the contaminated waste;

heating the oven under said conditions of sterilization in such a way that the hot-melt plastic material arranged in the disposable container melts and encloses the waste, thereby making the disposable container and the waste non-reusable; and removing from the oven the container containing the waste which has been sterilized and enclosed by the hot-melt plastic material, and disposing of said container.

15. A method according to claim 14, wherein the predetermined sterilization temperature is situated between 50° C. and 300° C.

16. A method according to claim 14, wherein the predetermined duration of sterilization is between 15 and 120 minutes.

17. An assembly according to claim 1, wherein the filter is made of a material which is resistant to the conditions of sterilization.

18. A method according to claim 14, wherein the filter is made of a material which is resistant to the conditions of sterilization.

19. An assembly according to claim 1, wherein the cover includes a male part comprising a retainer ring, and the container includes a female part comprising a flange, and wherein a thermosetting material is arranged on said flange.

20. An assembly according to claim 1, wherein the cover includes a male part comprising a retaining ring, and the container includes a female part comprising a flange, and wherein a thermosetting material is arranged on said retainer ring.

21. An assembly according to claim 1, wherein the container includes an introduction opening having a non-return flap to introduce the waste into the container.

22. A method according to claim 14, wherein said sealing step is effected by a thermosetting material arranged between a retainer ring of said cover and a flange of said container.

* * * * *